United States Patent [19]
Archibald et al.

[11] Patent Number: 6,011,177
[45] Date of Patent: Jan. 4, 2000

[54] PROCESS FOR 4-SULFONAMIDOLPHENYL HYDRAZINES

[75] Inventors: Thomas G. Archibald, Fair Oaks; James C. Barnard, Shingle Springs, both of Calif.

[73] Assignee: Aerojet-General Corporation, Rancho Cordova, Calif.

[21] Appl. No.: 08/978,965

[22] Filed: Nov. 26, 1997

[51] Int. Cl.$^7$ .................................................. C07C 303/40
[52] U.S. Cl. .............................................................. 564/81
[58] Field of Search .................................................. 564/81

[56] References Cited

U.S. PATENT DOCUMENTS

| | | | |
|---|---|---|---|
| 3,476,763 | 11/1969 | Monbaliu | 260/294.8 |
| 3,839,325 | 10/1974 | Hoffstadt | 514/406 |
| 5,563,165 | 10/1996 | Talley et al. | 260/239.7 |

*Primary Examiner*—Peter O'Sullivan
*Attorney, Agent, or Firm*—Townsend and Townsend and Crew LLP

[57] ABSTRACT

4-Sulfonamidophenyl hydrazines are prepared by reaction between the hydrazine, optionally substituted, and the corresponding 4-substituted benzenesulfonamides, where the 4-substitution is an appropriate leaving group, in the presence of water and the absence of dimethyl sulfoxide as a solvent. The result is a product of unusually high purity.

30 Claims, No Drawings

PROCESS FOR 4-SULFONAMIDOLPHENYL HYDRAZINES

BACKGROUND OF THE INVENTION

1. Field of the Invention

This invention lies in the technology of synthetic processes for 4-sulfonamidophenyl hydrazines.

2. Description of the Prior Art

The compound 4-sulfonamidophenyl hydrazine and its various derivatives and analogs are useful for a variety of purposes. Some of these compounds are intermediates in the production of substituted phenyl pyrazolones, which serve a wide range of utilities extending from magenta color formers used in color photography to non-steroidal antiinflammatory drugs (NSAIDs) used for the inhibition of prostaglandins in the control of inflammation arising from arthritis and other physiological conditions. Disclosure of the use of 4-sulfonamidophenyl hydrazines in the synthesis of magenta color formers appears in U.S. Pat. No. 3,839,325 to Hoffstadt, Walter F. (GAF Corporation), issued Oct. 1, 1974, while disclosure of the use of these compounds in the synthesis of NSAIDs appears in U.S. Pat. No. 5,563,165 to Tally, John J., et al. (G. D. Searle & Co.), issued Oct. 8, 1996. The NSAIDs formed from 4-sulfonamidophenyl hydrazines are particularly useful for the selective inhibition of COX-2 relative to COX-1, both of which are cyclooxygenase enzymes that play key roles in the biosynthesis of prostaglandins.

The substituted phenyl pyrazolones that are used as COX-2 inhibitors and other therapeutic drugs often require administration in large doses over extended periods of time. It is therefore important that the drug and its intermediate be highly pure and capable of being synthesized free of impurities, in addition to being economical.

The most cost-effective synthesis of the 4-sulfonamidophenyl hydrazine intermediate is one in which the starting material is 4-chlorobenzenesulfonamide, since this material is both commercially available and readily prepared from the chlorosulfonation of chlorobenzene followed by reaction with ammonium hydroxide. A description of the conversion of 4-chlorobenzenesulfonamide (and its substituted analogs) to 4-sulfonamidophenyl hydrazine (and its substituted analogs) appears in the Hoffstadt patent cited above. The Hoffstadt process calls for the use of dimethyl sulfoxide (DMSO) as an aprotic dipolar solvent to enhance the nucleophilic character of the hydrazine. Unfortunately, the hydrazine, in addition to reacting with the 4-chlorobenzenesulfonamide, also reduced the DMSO to dimethyl sulfide and other by-products, resulting in a critically impure product.

A process that takes advantage of the low cost and availability of 4-chlorobenzenesulfonamide and yet produces a high product yield with little or no impurities is therefore needed.

SUMMARY OF THE INVENTION

It has now been discovered that 4-sulfonamidophenyl hydrazines can be prepared from an appropriate hydrazine and the corresponding benzenesulfonamide substituted with a leaving group at the 4-position, to result in a product of high yield and high purity, by eliminating the use of dimethyl sulfoxide as solvent, and preferably by avoiding the use of all organic solvents, i.e., performing the reaction in a reaction medium that is devoid of solvents other than water. When water is present in the reaction medium, the reaction successfully proceeds at a rapid rate with little or no by-product formation. When the product is further converted to the more stable hydrochloride, it is readily purified by recrystallization. Thus, the invention permits use of a relatively inexpensive starting material and produces a product of high purity that permits recycling of the recrystallization solvent.

These and other features, objects, and advantages of the invention are presented in detail in the description that follows.

DETAILED DESCRIPTION OF THE INVENTION AND PREFERRED EMBODIMENTS

The 4-sulfonamidophenyl hydrazines whose preparation is the subject of this invention are those having the formula:

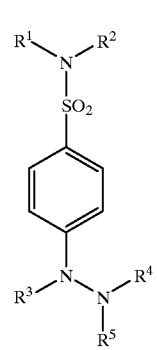

(I)

The corresponding 4-substituted benzenesulfonamides are those having the formula:

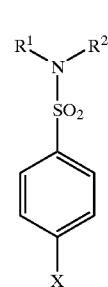

(II)

In Formulas I and II, the symbols $R^1$ and $R^2$ represent substituent groups, either individually in which case the sulfonamido nitrogen atom is an acyclic secondary or tertiary amine, or together in which $R^1$ and $R^2$ are combined to form a single divalent moiety and to form a nitrogen-containing heterocyclic with the sulfonamido nitrogen atom, the latter thereby forming a cyclic amine.

When taken individually, $R^1$ and $R^2$ are either the same or different (and are thus referred to herein as being "independently selected") and are either hydrogen, alkyl, cycloalkyl, alkaryl, aralkyl or aryl. The term "alkyl" as used herein includes saturated groups, unsaturated groups, straight-chain groups and branched-chain groups. A preferred carbon atom range for the alkyl groups is 1 to 6 carbon atoms per group, with 1 to 3 carbon atoms preferred. Cycloalkyl groups are nonaromatic cyclic groups in which the ring atoms are all carbon atoms. Examples of cycloalkyl groups are cyclopentyl, cyclopentenyl, cyclohexyl, and cyclohexenyl. The term "aryl" includes any conjugated (aromatic) sixmembered carbon atom ring or two or more such rings fused. The preferred aryl group is the phenyl group. A preferred subgenus for both $R^1$ and $R^2$ is hydrogen and alkyl, more preferably hydrogen and $C_1$–$C_3$ alkyl, and most preferably hydrogen.

When combined with the sulfonamido nitrogen to form a heterocyclic ring, the heterocyclic ring contains from 3 to 7 ring atoms in addition to the sulfonamido nitrogen, the ring atoms can be substituted or unsubstituted, the ring can be saturated or unsaturated, and the ring can contain the sulfonamido nitrogen as the sole heteroatom, or one or more additional heteroatoms such as S atom(s), (O) atoms, or further N atom(s). Examples of heterocyclic rings within this group are pyrrolydyl, pyrryl, pyrrolinyl, piperidyl, oxazolidyl, thiazolidyl, imidazolinyl, imidazolidinyl, pyrazolinyl, pyrazolidinyl, piperazinyl, and morpholinyl.

The formula for the hydrazine used as a starting material is $R^3$—NH—$NR^4R^5$. In both the hydrazine formula and in Formula I, $R^3$, $R^4$ and $R^5$ are either the same or different (and are thus referred to herein as being "independently selected") and are either H, alkyl, aryl, aralkyl, or alkaryl, with the limitation that the total number of carbon atoms in $R^3$, $R^4$ and $R^5$ is seven or less. A preferred subgenus for $R^3$, $R^4$ and $R^5$ is H, alkyl, and aryl, with H and alkyl more preferred. Compounds in which $R^3$, $R^4$ and $R^5$ are each H are the most preferred.

The symbol X in Formula II represents a leaving group active in an aromatic nucleophilic substitution. Such leaving groups are well known among synthesis chemists. Examples are F, $NO_2$, OTs (p-toluenesulfonyl), phenylsulfenyl, chloro, bromo, iodo, aryloxy, alkylthio, and alkylsulfinyl. Preferred among these is chloro.

Water can be present in the reaction medium either as water of hydration of the hydrazine monohydrate, or as free water. The amount of water included in the reaction medium is not critical to the invention, and can vary while still achieving beneficial results. Water is conveniently included by simply using hydrazine monohydrate in place of hydrazine, although water can be added separately. In hydrazine hydrate, the water of hydration constitutes 36% by weight (a hydrazine:water weight ratio of 64:36). In preferred reaction media in accordance with this invention, the weight ratio of hydrazine to water is from about 15:85 to about 75:25. In reaction media that are more preferred, the weight ratio of hydrazine to water is from about 25:75 to about 64:36, and most preferably from about 50:50 to about 64:36.

The mole ratio of the hydrazine to the 4-substituted benzenesulfonamide can vary widely while still providing effective results. Since the cost of the hydrazine is low compared to the 4-substituted benzenesulfonamide and the reaction rate increases with the hydrazine concentration consistent with a second-order reaction, the hydrazine is preferably used in excess. The mole ratio of hydrazine to the 4-substituted benzenesulfonamide is preferably from about 2:1 to about 20:1, and more preferably from about 5:1 to about 10:1.

The reaction is best conducted at a temperature sufficiently high that all reactants are dissolved in the reaction medium, thus forming an entirely liquid reaction medium. The reaction is preferably performed at reflux, particularly when water is the only solvent present. When using hydrazine monohydrate as the source of both hydrazine and water (a hydrazine:water weight ratio of 64:36), the reflux temperature is approximately the boiling point of hydrazine monohydrate, which is 119° C. The reaction can be performed at ambient pressure or at a higher pressure. Ambient (atmospheric) pressure is preferred.

The reaction can be performed in a batchwise manner, a continuous manner, or a process that includes a combination of both batchwise and continuous segments. Batchwise reactions are preferred. The reaction residence time will vary depending on such factors as temperature, hydrazine:water ratio, and hydrazine:benzenesulfonamide ratio. The progress of the reaction is readily monitored by sampling and analysis such as chromatography or NMR. In general, and particularly in the preferred procedures and conditions described above, the reaction will be substantially complete in a period of time ranging from about twenty hours to about 50 hours.

Recovery of the product from the reaction mixture is achieved by conventional techniques. A particularly convenient technique is to cool the reaction mixture to a temperature at which the product precipitates. In the system where water is the only solvent, effective recovery of the product can be achieved by cooling to a temperature of about 10° C. or below, and preferably about 5° C. or below, and adding additional water. The degree of cooling and amount of water added are preferably sufficient to precipitate at least about 95% of the free base. The precipitated free base is then recovered by filtration, centrifugation, decantation or any other conventional technique for separating solids from liquids.

The free base product is readily converted to the hydrochloride by reaction with hydrogen chloride, preferably aqueous hydrochloric acid. Since the hydrochloride is more soluble in water than the free base, the solid product from the reaction to form the free base is preferably washed in a nonaqueous solvent prior to the reaction to form the hydrochloride. For this wash, it is preferred to use a nonaqueous solvent that dissolves the starting 4-substituted benzenesulfonamide in order to remove any residual amounts of this starting material before the hydrochloride reaction. A lower alkyl alcohol such as a $C_1$–$C_3$ alkanol is an example of a solvent that can be used effectively for this purpose. Methanol and ethanol are preferred, with methanol the most preferred in terms of convenience and cost.

In the hydrochloride reaction, the hydrochloric acid is preferably added as concentrated aqueous hydrochloric acid of at least about 25% by weight. Full strength hydrochloric acid at 37% by weight can be used, although additional water may be useful in dissolving the reaction materials. The hydrochlorination is preferably performed at an elevated temperature, particularly at least 50° C., and most preferably within the range of about 65° C. to about 90° C. Recovery of the hydrochloride can be achieved by any conventional means. The preferred method in the context of this invention is by cooling the reaction mixture to a temperature at which the hydrochloride precipitates out. To enhance precipitation, the reaction mixture can contain an appropriate nonaqueous solvent. A convenient solvent is the same solvent used for the solvent wash of the free base prior to the hydrochlorination reaction. Thus, a $C_1$–$C_3$ alkanol, preferably methanol or ethanol, is conveniently used.

Recovery of the precipitated hydrochloride is achievable as well by conventional means, including filtration, centrifugation, and decanting. To improve the product purity, the recovered hydrochloride can be recrystallized from fresh solvent, or from recycled solvent.

The following examples are offered for purposes of illustration only.

EXAMPLE 1

This example illustrates a batch process for the preparation of 4-sulfonamidophenyl hydrazine hydrochloride (unsubstituted at the amido N atom: $R^1=R^2=H$) from 4-chlorobenzenesulfonamide and hydrazine.

A 2-liter glass reactor fitted with a reflux condenser, thermometer, heating mantle and magnetic stirrer was charged with 4-chlorobenzenesulfonamide (500 g, 2.61 moles) and hydrazine monohydrate (1,000 g, 20.0 moles, 64% water by weight). The mixture was heated to reflux (121° C.) over about 30 minutes and maintained at reflux for 40 hours, at which time analysis by NMR indicated that 93% conversion of the 4-chlorobenzenesulfonamide had occurred. While the reaction mixture was maintained at a temperature of at least 90° C., the reaction mixture was filtered into a 5-liter reactor equipped with a mechanical stirrer, thermometer, reflux condenser, and heating mantle, then diluted with water (1500 g) while maintaining a temperature of at least about 80° C. With continuous stirring, the diluted product was crystallized by cooling to 5° C. over a two-hour period.

The product mixture was filtered, leaving a filter cake of about 1,600 mL in volume (3.3 inches (8.4 cm) in depth and 28 square inches (181 square cm) in area). The filtration required about 2.5 minutes. Filtration was followed by a cold water displacement wash (2,500 g, 5 minutes) and a 0° C. methanol displacement wash (750 mL, 2.8 minutes). Titration of the filtrate from the methanol displacement wash with hydrochloric acid revealed that the filtrate contained only 0.06% hydrazine.

The filter cake remaining after the displacement washes was added to methanol (1,700 mL) and 37% hydrochloric acid (2.75 g, 2.84 moles) to form a slurry. The addition caused an exotherm from 20° C. to 34° C. The slurry was then heated to 71° C., and 300 mL of water was added to dissolve the hydrochloride product. The solution was then stirred for 15 minutes and cooled to −6° C. over two hours, causing the hydrochloride to precipitate. The precipitate was filtered over about 20 seconds, forming a filter cake 740 mL in volume and 1.6 inches (4.1 cm) in thickness.

The hydrochloride filter cake was displacement washed with methanol at −10° C. (650 mL), leaving a slightly off-white cake (525 g). The resulting cake was vacuum dried over two hours to a constant weight of 404 g (1.806 moles). This corresponds to a 69.2% yield. The purity was determined by titration to be 99.0%, with less than 0.1% starting material remaining as indicated by NMR.

The combined filtrates weighed 2,920 g, and contained 3.1% product (90 g), representing 15% of the theoretical yield.

EXAMPLE 2

This example illustrates a batch process for the preparation of 4-sulfonamidophenyl hydrazine hydrochloride from 4-chlorobenzenesulfonamide and hydrazine as in Example 1, with the hydrochloride stage performed in a succession of batches. Rather than using fresh methanol as the solvent for each batch of the hydrochloride stage, the solvent used was a recycled mixture of filtrate from the hydrochloride product filter cake (i.e., the mother liquor filtrate) and filtrate from the methanol wash, both from the preceding batch. The purpose was to determine whether the solvent could be recycled repeatedly without detriment to product yield and purity, since product purity was so high and the quantity of unreacted material in the solvent so low.

The crude 4-sulfonamidophenyl hydrazine (i.e., the free base) was prepared in two batches, the first providing five 200-g portions of a wet filter cake, and the second providing three 200-g portions. These portions were used in succession, beginning with the five from the first batch. For the hydrochlorination stages, the solvent used for the first 200-g wet cake portion was 350 mL of methanol plus 90 mL water. A slurry of the free base filter cake and this methanol/water mixture was formed, and aqueous HCl (37%, 55 g) was added with agitation. A sample was taken from the slurry to check pH, and the sample was then returned to the slurry. Extra water was added as needed to dissolve the solids when heated to reflux, and the mixture was then refluxed until all solids dissolved. The resulting solution was then cooled to −5° C., filtered, washed with methanol, and dried.

For subsequent wet cake portions of free base, the filtrates (i.e., combined portions of both the mother liquor (recrystallization) filtrate and the methanol wash filtrate) were used in place of the methanol/water mixture. To avoid an accumulation of water in the reaction medium from the need for fresh HCl for each batch, a portion of the mother liquor was discarded. Otherwise the procedure was the same as that used with the first free base wet cake portion, with variations in the amounts added, as indicated in the table below, which lists the amounts used and the results for each batch. In this table, the abbreviation "MeOH" is used for methanol, the abbreviation "4-SAPH·HCl" is used for 4-sulfonamidophenyl hydrazine hydrochloride, and the abbreviation "CBS" is used for 4-chlorobenzenesulfonamide.

EXAMPLE 2

Hydrochloride Stage Recycle—Materials and Results

| | | Slurry Composition | | | | Mother Liquor Filtrate Analysis (remainder: methanol) | | |
| --- | --- | --- | --- | --- | --- | --- | --- | --- |
| (1) Run No. | (2) Initial MeOH Charge or Recycled Filtrates from (11) and (12) (mL) | (3) Fresh H$_2$O Added (mL) | (4) 37% HCl Added (g) | (5) pH | (6) % Water | (7) % 4-SAPH.HCl | (8) % CBS | (9) Volume (mL) |
| 1 | 350 | 90 | 55 | 2 | 24.1 | 4.2 | 0.17 | 363 |
| 2 | 410 | 10 | 55 | 2.5 | 24.8 | 4.7 | 0.17 | 368 |
| 3 | 450 | 10 | 55 | 2.3 | 25.1 | 4.0 | 0.22 | 390 |
| 4 | 410 | 20 | 55 | 2.2 | 26.7 | 4.5 | 0.29 | 475 |
| 5 | 430 | 20 | 55 | 1.9 | 26.0 | 3.7 | 0.25 | 295 |
| 6 | 450 | 10 | 55 | 1.8 | 27.7 | 3.5 | 0.12 | 460 |
| 7 | 440 | 10 | 51.2 | 1.5 | 24.8 | 3.3 | 0.42 | 390 |

-continued

| | Slurry Composition | | | | Mother Liquor Filtrate Analysis (remainder: methanol) | | | |
|---|---|---|---|---|---|---|---|---|
| (1) Run No. | (2) Initial MeOH Charge or Recycled Filtrates from (11) and (12) (mL) | (3) Fresh H₂O Added (mL) | (4) 37% HCl Added (g) | (5) pH | (6) % Water | (7) % 4-SAPH.HCl | (8) % CBS | (9) Volume (mL) |
| 8 | 440 | 10 | 48 | 1.6 | 26.5 | 3.8 | 0.29 | 390 |

Continuation:

| | (10) | Methanol Wash | | Mother Liquor Discarded | | Product 4-SAPH.HCl | | | |
|---|---|---|---|---|---|---|---|---|---|
| Run No. | Mother Liquor Recycled (mL) | (11) Wash Volume (mL) | (12) Filtrate Volume (mL) | (13) Total Volume (mL) | (14) 4-SAPH.HCl (g) | (15) Wet Cake (g) | (16) Dried (g) | (17) Purity by titration (%) | (18) Percent Recovery |
| 1 | 210 | 125 | 200 | 153 | 5.35 | 188 | 102.8 | 100.6 | 96 |
| 2 | 190 | 125 | 260 | 178 | 7.19 | 155 | 115.5 | 100.6 | 95 |
| 3 | 210 | 120 | 200 | 180 | 6.19 | 179 | 116.5 | | 95 |
| 4 | 240 | 120 | 190 | 235 | 9.09 | 162 | 112.7 | 100.5 | 93 |
| 5 | 165 | 120 | 290 | 130 | 4.14 | 205 | 111.1 | | 97 |
| 6 | 280 | 100 | 180 | 180 | 5.42 | 153 | 102.4 | 100.6 | 96 |
| 7 | 210 | 100 | 230 | 180 | 5.11 | 176 | 102.6 | | 96 |
| 8 | 0 | 100 | 205 | 595 | 19.44 | 196 | 103.6 | 100.1 | 84 |

While the CBS starting material was present in the filtrates at levels ranging from 0.17% to 0.42% as shown in the above table, no CBS was detected in the final product by NMR, which has a detection limit of about 0.1%. Titration of the product yielded purities ranging from 100.1% to 100.6% (column 17), indicating no deterioration of product quality.

The foregoing is offered primarily for purposes of illustration. It will be readily apparent to those skilled in the art that the proportions, the operating conditions, the order and method of performing the procedural steps, and other system parameters described herein may be further modified or substituted in various ways without departing from the spirit and scope of the invention.

We claim:

1. A process for the preparation of a 4-sulfonamidophenyl hydrazine having the formula

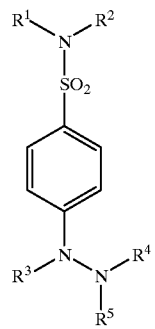

in which:

$R^1$ and $R^2$ are independently selected from the group consisting of hydrogen, alkyl, cycloalkyl, alkaryl, aralkyl and aryl, or $R^1$ and $R^2$ together with the nitrogen atom form a nitrogen-containing heterocyclic ring, and $R^3$, $R^4$ and $R^5$ are independently selected from the group consisting of hydrogen, alkyl, aryl, aralkyl, and alkaryl, with the proviso that the total number of carbon atoms in $R^3$, $R^4$ and $R^5$ is seven or less, said process comprising reacting a 4-substituted benzenesulfonamide having the formula

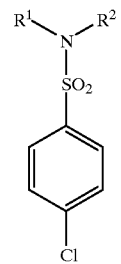

in which X is a leaving group active in an aromatic nucleophilic substitution, with a hydrazine of the formula $R^3$—NH—$NR^4R^5$ in a liquid-phase reaction medium containing water and in the absence of dimethyl sulfoxide, to form said 4-sulfonamidophenyl hydrazine.

2. A process in accordance with claim 1 in which said liquid-phase reaction medium is devoid of solvents other than water.

3. A process in accordance with claim 1 in which said hydrazine and said water are present in a weight ratio of from about 15:85 to about 75:25.

4. A process in accordance with claim 1 in which said hydrazine and said water are present in a weight ratio of from about 25:75 to about 64:36.

5. A process in accordance with claim 1 in which $R^1$ and $R^2$ are independently selected from the group consisting of hydrogen and alkyl.

6. A process in accordance with claim 1 in which $R^1$ and $R^2$ are both hydrogen.

7. A process in accordance with claim 1 in which $R^3$, $R^4$ and $R^5$ are independently selected from the group consisting of H and alkyl.

8. A process in accordance with claim 1 in which $R^3$, $R^4$ and $R^5$ are all H.

9. A process in accordance with claim 1 in which said hydrazine and said 4-substituted benzenesulfonamide are present in said liquid reaction medium at a hydrazine:benzenesulfonamide mole ratio of from about 2:1 to about 20:1.

10. A process in accordance with claim 1 in which said hydrazine and said 4-substituted benzenesulfonamide are present in said liquid reaction medium at a hydrazine:benzenesulfonamide mole ratio of from about 5:1 to about 10:1.

11. A process in accordance with claim 1 in which said hydrazine and said 4-substituted benzenesulfonamide is 4-chlorobenzenesulfonamide.

12. A process in accordance with claim 1 in which said reaction medium is devoid of solvents other than water, and said reaction is conducted at reflux temperature.

13. A process for the preparation of a 4-sulfonamidophenyl hydrazine hydrochloride having the formula

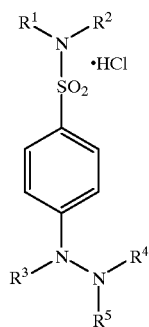

in which:
R$^1$ and R$^2$ are independently selected from the group consisting of hydrogen, alkyl, cycloalkyl, alkaryl, aralkyl and aryl, or R$^1$ and R$^2$ together with the nitrogen atom form a nitrogen-containing heterocyclic ring, and
R$^3$, R$^4$ and R$^5$ are independently selected from the group consisting of hydrogen, alkyl, aryl, aralkyl, and alkaryl, with the proviso that the total number of carbon atoms in R$^3$, R$^4$ and R$^5$ is seven or less,
said process comprising:
(a) reacting a 4-substituted benzenesulfonamide having the formula

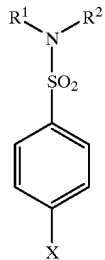

in which X is a leaving group active in an aromatic nucleophilic substitution, with hydrazine of the formula R$^3$—NH—NR$^4$R$^5$ in a liquid-phase reaction medium containing water and in the absence of dimethyl sulfoxide, to form a 4-sulfonamidophenyl hydrazine;

(b) recovering said 4-sulfonamidophenyl hydrazine from said liquid-phase reaction medium; and
(c) reacting said 4-sulfonamidophenyl hydrazine thus recovered with HCl to form said 4-sulfonamidophenyl hydrazine hydrochloride.

14. A process in accordance with claim 13 in which said liquid-phase reaction medium is devoid of solvents other than water.

15. A process in accordance with claim 13 in which said hydrazine and said water are present in said liquid-phase reaction medium in a weight ratio of from about 15:85 to about 75:25.

16. A process in accordance with claim 13 in which said hydrazine and said water are present in said liquid-phase reaction medium in a weight ratio of from about 25:75 to about 64:36.

17. A process in accordance with claim 13 in which $R^1$ and $R^2$ are independently selected from the group consisting of hydrogen and alkyl.

18. A process in accordance with claim 13 in which $R^1$ and $R^2$ are both hydrogen.

19. A process in accordance with claim 13 in which $R^3$, $R^4$ and $R^5$ are independently selected from the group consisting of H and alkyl.

20. A process in accordance with claim 13 in which $R^3$, $R^4$ and $R^5$ are all H.

21. A process in accordance with claim 13 in which said hydrazine and said 4-chlorobenzenesulfonamide are present in said liquid reaction medium at a hydrazine:benzenesulfonamide mole ratio of from about 2:1 to about 20:1.

22. A process in accordance with claim 13 in which said hydrazine and said 4chlorobenzenesulfonamide are present in said liquid reaction medium at a hydrazine:benzenesulfonamide mole ratio of from about 5:1 to about 10:1.

23. A process in accordance with claim 13 in which said hydrazine and said 4-substituted benzenesulfonamide is 4-chlorobenzenesulfonamide.

24. A process in accordance with claim 13 in which said reaction medium is devoid of solvents other than water, and said reaction is conducted at reflux temperature.

25. A process in accordance with claim 13 in which $R^1$ and $R^2$ are both hydrogen, said reaction medium is devoid of solvents other than water, and said reaction is conducted at reflux temperature.

26. A process in accordance with claim 25 in which (b) is performed by adding water to said liquid reaction medium, cooling said liquid reaction medium sufficiently to precipitate at least about 95% of said 4-sulfonamidophenyl hydrazine, and isolating said precipitated 4-sulfonamidophenyl hydrazine from substantially all liquids remaining from said liquid-phase reaction mixture.

27. A process in accordance with claim 25 in which (c) is performed by dissolving said 4-sulfonamidophenyl hydrazine in a mixture of a $C_1$–$C_3$ alkanol and aqueous hydrochloric acid at a temperature of at least about 50° C. to form said 4-sulfonamidophenyl hydrazine hydrochloride in a liquid solution, cooling said mixture to a temperature sufficiently to precipitate at least about 75% of said 4-sulfonamidophenyl hydrazine hydrochloride, and isolating said precipitated 4-sulfonamidophenyl hydrazine hydrochloride from substantially all liquids remaining from said liquid solution.

28. A process in accordance with claim 27 in which said $C_1$–$C_3$ alkanol is methanol or ethanol and said aqueous hydrochloric acid is at least about 10% HCl by weight.

29. A process in accordance with claim 27 in which said $C_1$–$C_3$ alkanol s methanol, and said aqueous hydrochloric acid is at least about 25% HCl by weight, and (c) is performed at a temperature of from about 65° C. to about 90° C.

30. A process in accordance with claim 27 performed in at least two successive batches, in which at least a portion of said liquids remaining after isolation of said precipitated 4-sulfonamidophenyl hydrazine hydrochloride from one batch is used to dissolve 4-sulfonamidophenyl hydrazine from a subsequent batch.

* * * * *